(12) United States Patent
Chen et al.

(10) Patent No.: US 10,716,956 B2
(45) Date of Patent: Jul. 21, 2020

(54) RADIOTHERAPEUTIC DEVICE

(71) Applicant: Xi'an Cyber Medical Technology Co., Ltd., Xi'an (CN)

(72) Inventors: Fangzheng Chen, Xi'an (CN); Haifeng Liu, Xi'an (CN)

(73) Assignee: OUR UNITED CORPORATION, Xi'an (JP)

( * ) Notice: Subject to any disclaimer, the term of this patent is extended or adjusted under 35 U.S.C. 154(b) by 200 days.

(21) Appl. No.: 15/351,502

(22) Filed: Nov. 15, 2016

(65) Prior Publication Data

US 2018/0133517 A1 May 17, 2018
US 2020/0121956 A9 Apr. 23, 2020

Related U.S. Application Data

(63) Continuation-in-part of application No. 14/437,333, filed on Apr. 21, 2015, now Pat. No. 9,526,919, which is a continuation of application No. 15/350,143, filed on Nov. 14, 2016, now Pat. No. 9,694,210.

(51) Int. Cl.
*A61N 5/00* (2006.01)
*A61N 5/10* (2006.01)

(52) U.S. Cl.
CPC .................................. *A61N 5/1081* (2013.01)

(58) Field of Classification Search
CPC ................ A61N 5/1081; A61N 5/1084; A61N 2005/1061
See application file for complete search history.

(56) References Cited

U.S. PATENT DOCUMENTS

| | | | |
|---|---|---|---|
| 5,537,452 A | 7/1996 | Shepherd et al. | |
| 5,818,902 A | 10/1998 | Yu | |
| 7,280,633 B2 | 10/2007 | Cheng et al. | |
| 7,835,492 B1 | 11/2010 | Sahadevan | |
| 7,902,530 B1 | 3/2011 | Sahadevan | |
| 8,139,714 B1 | 3/2012 | Sahadevan | |
| 8,173,983 B1 | 5/2012 | Sahadevan | |
| 2002/0006182 A1 | 1/2002 | Kim et al. | |
| 2004/0013225 A1* | 1/2004 | Gregerson | A61B 6/032 378/19 |

(Continued)

FOREIGN PATENT DOCUMENTS

| | | |
|---|---|---|
| CN | 1275410 A | 12/2000 |
| CN | 1355055 A | 6/2002 |

(Continued)

OTHER PUBLICATIONS

International search report of PCT application No. PCT/CN2013/086462 dated Aug. 13, 2014.

(Continued)

*Primary Examiner* — Dani Fox
(74) *Attorney, Agent, or Firm* — Daniel J. Chalker; Edwin S. Flores; Chalker Flores, LLP

(57) ABSTRACT

The present disclosure discloses a radiotherapeutic device. The radiotherapeutic device includes a gantry, a detector and a slide driving unit. The slide driving unit includes a sliding guide rail, a driving apparatus and a movable block. The detector is fixed on the movable block. The movable block drives the detector to slide along the sliding guide rail driven by the driving apparatus.

15 Claims, 11 Drawing Sheets

(56) References Cited

U.S. PATENT DOCUMENTS

| | | | |
|---|---|---|---|
| 2013/0114790 A1 | 5/2013 | Fabrizio | |
| 2016/0081635 A1* | 3/2016 | Divine | A61B 6/06 378/19 |
| 2016/0114191 A1* | 4/2016 | Sankey | A61N 5/1049 378/62 |

FOREIGN PATENT DOCUMENTS

| | | |
|---|---|---|
| CN | 1565670 A | 1/2005 |
| CN | 1643371 A | 7/2005 |
| CN | 1919372 A | 2/2007 |
| CN | 102525509 A | 7/2012 |
| CN | 102688558 A | 9/2012 |
| CN | 102698374 A | 10/2012 |
| CN | 202682584 U | 1/2013 |
| CN | 102939607 A | 2/2013 |
| CN | 103476340 A | 12/2013 |
| CN | 203408368 U | 1/2014 |
| CN | 104771839 A | 7/2015 |
| CN | 105167796 A | 12/2015 |
| JP | H03293600 A | 12/1991 |
| JP | 2002263094 A | 9/2002 |

OTHER PUBLICATIONS

First office action of Chinese application No. 201380004392.2 dated Nov. 21, 2016.
Second office action of Chinese application No. 201380004392.2 dated May 25, 2017.
First office action of Chinese application No. 201711260030.6 dated Oct. 9, 2019.
Second office action of Chinese application No. 201711260030.6 dated Dec. 30, 2019.
Extended European search report of counterpart EP application No. 13896320.2 dated May 9, 2017.
Extended European search report of counterpart EP application No. 181989005 dated Mar. 18, 2019.
International search report of PCT application No. PCT/CN2016/105936 dated Aug. 3, 2017.

* cited by examiner

RADIOTHERAPEUTIC DEVICE

CROSS-REFERENCE TO RELATED APPLICATION

This application is a continuation-in-part of U.S. application Ser. No. 14/437,333, filed on Apr. 21, 2015, which is hereby incorporated by reference herein.

TECHNICAL FIELD

The invention relates to the technical field of medical equipment, and more particularly to a radiotherapeutic device.

BACKGROUND

Modern radiotherapy of cancer has begun to enter the era of precise treatment, therefore, to achieve accurate image guidance and control the absorbed dose of radiation to make a good treatment plan with a high degree of matching is very important. As shown in FIG. 1, the radiotherapeutic device in the prior art includes a gantry 904, a therapeutic head 900, and a first detector 901 corresponding to the therapeutic head 900, and a set of image guidance device comprising a cone beam generator 902 and a second detector 903 corresponding to the cone beam generator 902. Wherein the therapeutic head 900 emits therapeutic radiation for treatment of the tumor. The primary function of the first detector 901 is to detect whether the dose of the radiation emitted from the therapeutic head 900 matches the dose of the patient's treatment plan, i.e. dose verification. The image guidance system is configured to perform real-time positioning of the patient prior to treatment or during treatment, wherein the primary function of the second detector 903 is to detect the x-rays emitted by the cone beam generator 902 and passed through the patient, to form images of the regions related to the tumor.

The cost of the radiotherapeutic device will increase while employing multiple detectors since the price of the detector is high. In addition, the detector has a limited service life in a ray-irradiated environment and, and it is necessary to carry out overhaul or replacement of the multiple detectors in the future maintenance of the equipment, which further increases the cost.

SUMMARY

The present invention provides a radiotherapeutic device which is capable of performing functions such as dose verification or image guidance with fewer detectors.

In order to solve the above technical problems, the present invention adopts the following technical scheme:

A radiotherapeutic device comprises a gantry, a detector and a slide driving unit, wherein the slide driving unit comprises a sliding guide rail, a driving apparatus and a movable block, the detector is fixed on the movable block, the movable block drives the detector to slide along the sliding guide rail driven by the driving apparatus.

Since the radiotherapeutic device comprising the gantry, the detector and the slide driving unit, wherein the slide driving unit comprises the sliding guide rail, the driving apparatus and the movable block, the detector is fixed on the movable block. As such, the movable block can drive the detector to slide along the sliding guide rail driven by the driving apparatus, and the detector can move to different positions to receive radiation beams from different radiation heads, thus the arrangement of the detector can be reduced. Even if there are multiple radiation heads being employed, it is also possible to provide fewer detectors to detect the radiation of different radiation heads. Therefore, fewer detectors can be used to perform functions such as dose verification or image guidance, and a large amount of treatment space is saved. In addition, fewer detectors can greatly reduce the acquisition cost of treatment equipments and maintenance costs.

REFERENCE LABELS

10—radiation head, focused therapeutic head, 11—gantry, first radioactive source, 12—sliding guide rail, collimator, 13—therapeutic head, first radiation beam, 14—imaging head, 15—movable block, 16—detector, 18—driver, 19—first motivation portion, 20—second motivation portion, conformal therapeutic head, 21—first position, second radioactive source, 22—second position, multi-leaf collimator, 23—motor, scattered cone beam, 24—motor gear, 25—gear ring, 26—sliding portion, 27—sliding rail unit, 28—pulley, 29—sliding rail, 30—pulley base, 31—mounting base, tumor, 33—sliding groove, 34—first tensional screw, 35—second tensional screw, 36—first nut, 37—second nut, 38—first protection nut, 39—second protection nut, 40—baffle, gantry, 41—first motivation unit, 42—second motivation unit, 151—cover plate, 152—through hole, 100—radiotherapeutic device, 50—base, 60—treatment couch.

DETAILED DESCRIPTION

In the description of the present invention, it is to be understood that the terms "center", "transverse", "up", "down", "left", "right", "vertical", "horizontal", "top", "bottom", "inner", "outer" or the like is based on the orientation or positional relationship shown in the figures, and is only to facilitate the description of the invention and to simplify the description and not to indicate or imply that the claimed device or elements must have a particular orientation, be constructed and operated in a particular orientation, and therefore should not be construed as limiting the invention. Furthermore, the terms "first" and "second" are used for description purposes only and are not to be construed as indicating or implying a relative importance or implicitly indicating the number of technical features indicated. Thus, a feature that defines "first" and "second" may include one or more of the features, either expressly or implicitly. In the description of the present invention, "plurality" or "multiple" means two or more unless otherwise specified. In addition, the term "comprise" or "include" and its variants are intended to cover non-exclusive inclusion.

In the description of the invention, it should be noted that the terms "mounted", "connect", "dispose" shall be understood broadly, unless the context clearly dictates otherwise, for example, a fixed connection or a detachable connection, or integrated connection; and it can be mechanical or electrical connection or directly connected, it can also be indirectly connected through the intermediary or an internal communication between two components. It will be apparent to those skilled in the art that the specific meaning of the above-described terms may be used in the present invention.

The invention will now be described in further detail with reference to the accompanying drawings and the preferred embodiments.

Figure 2:
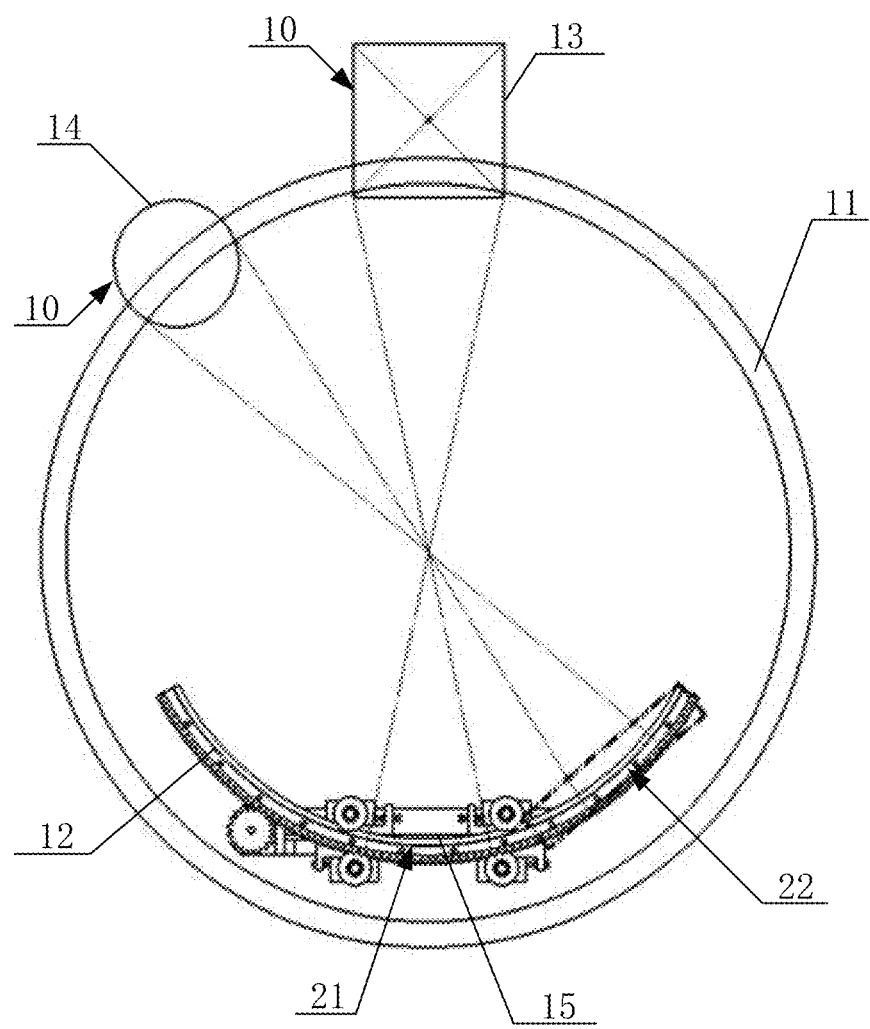
FIG. 2 is a schematic view of a radiotherapeutic device, according to an embodiment of the present disclosure.
Figure 3:
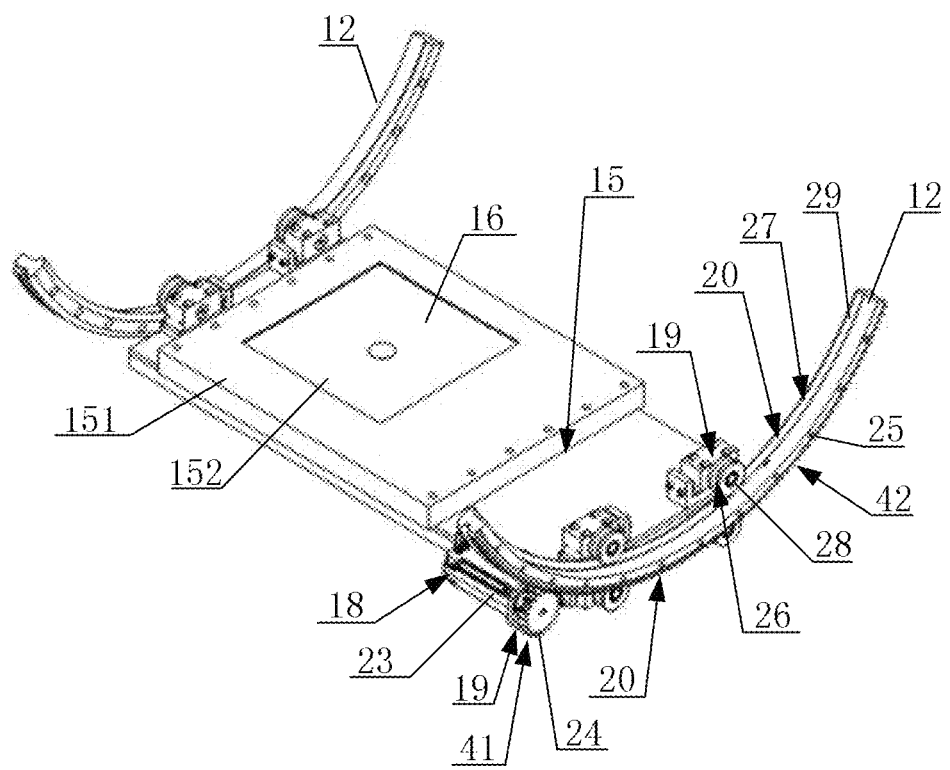
FIG. 3 is a schematic block diagram of part of the radiotherapeutic device, according to an embodiment of the present disclosure.

The present embodiment discloses a radiotherapeutic device, as shown in FIGS. 2 and 3, including a gantry 11, a detector 16 and a slide driving unit. The slide driving unit includes a sliding guide rail 12, a driving apparatus and a movable block 15. The detector 16 is fixed to the movable block 15. The movable block 15 drives the detector 16 to slide along the sliding guide rail 12 driven by the driving apparatus.

With this embodiment, the movable block 15 is moved along the sliding guide rail 12 driven by the driving apparatus, and the detector 16 on the movable block 15 also moves with the movable block 15, so that the detector 16 can move along the sliding guide rail 12. As such, the detector 16 can be moved to different positions to receive the radiation emitted by different radiation heads 10, and thus the arrangement of the detector 16 can be reduced. Even if there are multiple radiation heads 10 being employed, it is also possible to provide fewer detectors 16 to detect the radiation of different radiation heads 10. Therefore, fewer detectors 16 can be used to perform functions such as dose verification or image guidance, and a large amount of treatment space is saved. In addition, fewer detectors 16 can greatly reduce the acquisition cost of treatment equipments and maintenance costs.

As shown in FIGS. 2 and 3, an example is illustrated with the treatment apparatus including two radiation heads 10, a movable block 15, and a detector 16. As the two radiation heads 10 shown in FIG. 2, one of the radiation heads 10 which is shown in a rectangular shape is a therapeutic head 13, and the other one shown in a circle is an imaging head 14. As shown in FIG. 2, the movable block 15 is movable along the sliding guide rail 12, and the detector 16 is disposed on the movable block 15 and further moves along the sliding guide rail 12 as the movable block 15 is moved. When the movable block 15 is positioned on a first position 21, the radiation beams emitted by the therapeutic head 13 are irradiated to the detector 16, and when the detector 16 is positioned on the second position 22, the radiation beams emitted by the imaging head 14 are irradiated to the detector 16. Thus, the detector 16 can be moved relative to the therapeutic head 13 or the imaging head 14 respectively, and when the detector 16 is located at the first position 21 opposite the therapeutic head 13, the detector 16 can receive the radiation beams from the therapeutic head 13, which are subjected to dose verification. Or, in the course of treatment, the detector 16 receives radiation beams from the therapeutic head 13 which pass through the lesion of human body to image the lesion region. And when the detector 16 is located at the second position 22 opposite the imaging head 14, the detector 16 receives the radiation beams from the imaging head 14 which pass through the lesion of the human body, and then images the lesion region of the human body, for performing positioning of the patient prior to treatment or during treatment or tracking the tumor during treatment. Of course, during the course of treatment, when the detector 16 is on the first position 21, the detector 16 may also image the area of the lesion of the body based on the received radiation beams emitted by the therapeutic head 13. As such, when the detector 16 moves to the second position 22, after receiving radiation beams emitted from the imaging head 14 which passes through the human body lesion, the detector 16 may image the lesion region of the human body. Therefore, the lesion region can be imaged from different angles to form a 3D image of the lesion.

In this embodiment, FIG. 2 shows one embodiment of the present invention to explain the principle and effect of the present invention. For the radiotherapeutic device provided in the embodiments of the present invention, the number of the radiation heads and the detectors is not particularly limited. In the embodiment of the present invention, the therapeutic head is configured to emit high dosed radiation beams which pass through the lesion of the human body, and irradiate the tumor at the lesion so as to damage and necrotize the tissue of the tumor, so as to achieve therapeutic purposes. In this embodiment, it is exemplified that the therapeutic head can emit γ rays in MV grade, e.g., an accelerator, or includes a radioactive source, e.g., cobalt-60 or the like. The imaging head emits low-dosed radiation beams, and the intensity of the radiation beams are changed after passing through the lesion region of the human body, so as to determine the tumor image of the lesion region according to the intensity of the radiation beams. As an example, the imaging head is an X-ray tube that emits X-rays in KV level. In this embodiment, the number of the therapeutic head and the imaging head is not limited to one, but may be more than one therapeutic head and one imaging head. Besides, the radiotherapeutic device may only include two or more therapeutic heads or only includes two or more imaging heads or the like. The therapeutic head, the imaging head, and the like in the embodiments of the present invention are not limited, and are illustrated by the above-described example.

In the embodiments of the present invention, the number of the detectors may be one or more. When the number of detectors is more than one, it may be a plurality of detectors respectively disposed on corresponding movable blocks, or a plurality of detectors disposed on one movable block. As shown in the example, the number of the detector may be two, one of which is arranged on the movable block and the other is fixed to the gantry. The movement block may be provided with at least one, two, three, etc., and each movable block is provided with detector(s). The detector disposed on the movable block can be one, two, three etc. The length of the sliding guide rail can be set according to the needs, and the shape thereof can be arc or in circle, which can be set according to the location that the detector needs to reach.

Preferably, as shown in FIGS. 2 and 3, the detector 16 and the slide driving unit are disposed on the inner side of the gantry 11. The sliding guide rail 12 is arc shaped, and the center of the sliding guide rail 12 coincides with the center of the gantry 11. The path that the slide driving unit drives the detector 16 to move is an arc segment. Since the center of the sliding guide rail 12 coincides with the center of the gantry 11, the path of movement of the detector 16 is an arc-shaped section concentric with the gantry 11.

In this embodiment, as shown in FIG. 3, illustratively, the driving device includes a driver 18, a first motivation portion 19 disposed on the movable block, and a second motivation portion 20 disposed on the sliding guide rail 12. The first motivation portion 19 cooperates with the second motivation portion 20 to drive the movable block 15 sliding along the sliding guide rail 12. The driver 18 is functioned as the motivation source which drives the movable block 15 to slide on the sliding guide rail 12, and the cooperation of the first motivation portion 19 and the second motivation portion 20 may keep the movement of the movable block 15. Illustratively, the driver may be a motor, a hydraulic motivation unit, an air motor, etc. The first motivation portion may be an output unit of the motor, hydraulic motivation unit, air motor, such as a gear, a pulley, a slider and so on. The second motivation portion is in cooperation with the first motivation portion, and may be a gear, a rack, a guide rail, a slide rail and so on. In the present embodiment, the driver is fixed to the movable block, and the driver outputs the motivation to the first motivation portion, which cooperates with the second motivation portion on the sliding guide rail, thereby driving the movable block to slide on the sliding guide rail.

As shown in FIG. 3, for example, the first motivation portion 19 includes a first motivation unit 41, the second motivation portion 20 includes a second motivation unit 42, the first motivation unit 41 is connected to the movable block 15 and the driver 18 respectively, the second motivation unit 42 is disposed on the sliding guide rail 12, and the driver 18 drives the first motivation unit 41 to move on the second motivation unit 42 and further drives the movable block 15 to slide along the sliding guide rail 12. In this way, the driver 18 can transmit motivation to the first motivation unit 41, to move the first motivation unit 41 on the second motivation unit 42, and thereby drives the movable block 15 sliding along the sliding guide rail 12.

In the present embodiment, illustratively, as shown in FIG. 3, the driver 18 may be a motor 23 mounted on the movable block 15, the first motivation unit 41 may be a motor gear 24 mounted on the motor 23, the second motivation unit 42 may be a gear ring 25 disposed on the sliding guide rail 12. As such, the motor 23 outputs motivation to the motor gear 24, and the motor gear 24 engages with the gear ring 25 to move the movable block 15 on the sliding guide rail 12. In the present embodiment, the first motivation unit 41 may be a pulley, a slide, or the like, and the second motivation unit 42 may be a guide rail, a slide rail, or the like, and the above is only an example and is not specifically defined.

As shown in the FIG. 3, for example, the first motivation portion 19 further includes a sliding portion 26 disposed on the movable block 15, and the second motivation portion 20 further includes a sliding rail unit 27 mounted on the movable block 15. The sliding portion 26 is cooperated with the sliding rail unit 27 and slides relative to each other. The movable block 15 can be more stably mounted on the sliding guide rail 12 with the cooperation of the sliding portion 26 and the sliding rail unit 27, and the friction between the sliding portion 26 and sliding rail unit 27 can be reduced and the driving torque required is also smaller.

Figure 4:
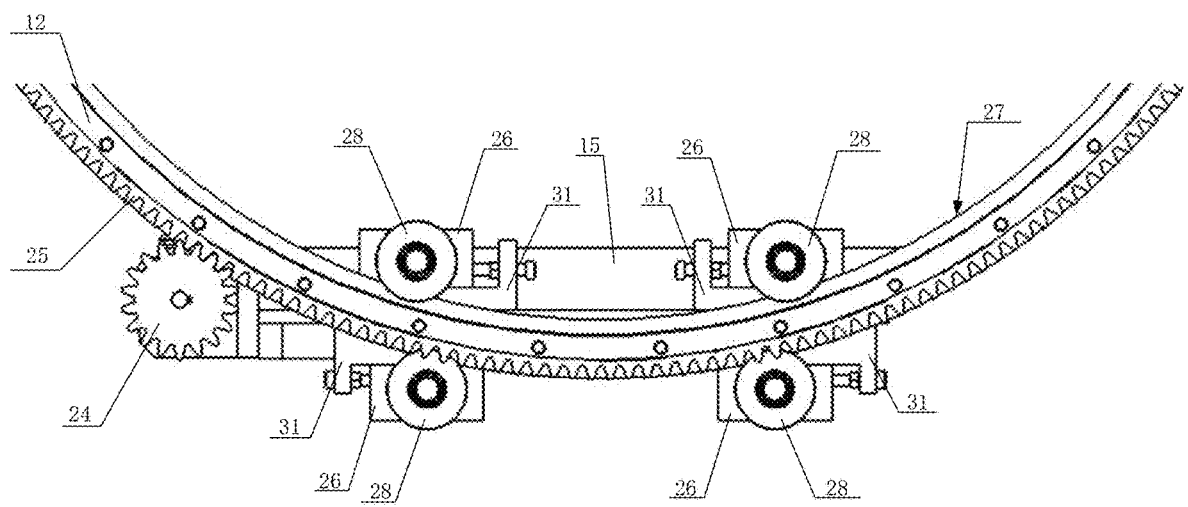
FIG. 4 is a schematic side view of the radiotherapeutic device, according to an embodiment of the present disclosure.

As shown in FIGS. 3 and 4, for example, the sliding portion 26 may be a pulley 28, and the sliding rail unit 27 may be a sliding rail 29 disposed on the sliding guide rail, e.g. a flange or groove, etc., to be cooperated with the pulley 28. Through sliding the pulley, the friction generated between the pulley and the sliding rail is a rolling friction, that is, the force of friction is small, the resistance while moving is less, and the drive torque used for driving the movable block is smaller. Illustratively, the sliding rail unit may include at least one groove disposed on the sliding guide rail, and the pulley is provided with a flange which engages with the groove; or the pulley is provided with at least one groove, and the sliding rail unit includes a flange disposed on the sliding guide rail that engages the groove. The number of the groove disposed on the pulley or the sliding guide rail may be one or more. Using the above-mentioned ways, the pulley can be prevented from derailment, and the cooperation between the pulley and the sliding rail is more stable. In the present embodiment, the first motivation portion and the sliding portion are disposed on the movable block, and the second motivation portion and the sliding portion are disposed on the sliding rail, so that the first motivation portion and the second motivation portion cooperate as a motivation transmission portion, to drive the movable block to move on the sliding rail. In addition, the cooperation between the sliding portion and the sliding rail unit can support the movable block to be stably disposed on the sliding guide rail, as well as reducing the friction between the sliding portion and the sliding rail unit, so that the movable block can slide on the sliding guide rail more stably and smoothly. In this way, the detector can be moved to the desired location faster and more accurately, ensuring the working efficiency and reliability of the detector.

Figure 5:
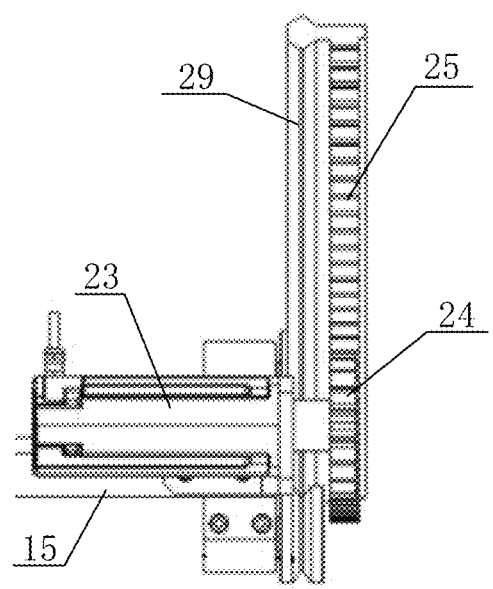
FIG. 5 is a schematic view of part of the radiotherapeutic device, according to an embodiment of the present disclosure.

In the present embodiment, illustratively, as shown in FIG. 5, the sliding rail unit is exemplified as a flange, and the second motivation portion is a gear ring. The flange and the gear ring may be arranged in such a manner that the gear ring is positioned on the outside of the flange, or the gear ring is located on the inner side of the flange. Besides, the sliding rail unit and the slide rail may be integrally formed, or the slide rail may be separately processed and assembled to the slide rail. The second transmission portion and the sliding guide rail may be integrally formed, or the second transmission part may be assembled with the sliding guide rail after being machined.

As shown in FIGS. 3 and 4, it is exemplified that at least one sliding portion 26 is disposed on each side of the sliding guide rail 12, and the two sliding portions 26 on both sides sandwich the sliding guide rail 12, makes it more stable for the movable block 15 to be fixed on the sliding guide rail 12. As shown in FIG. 4, for example, at least one pulley 28 may be disposed on each side of the sliding guide rail 12 so that the pulleys 28 on both sides can hold and fix the sliding guide rail 12, thereby making the movable block 15 to be mounted on the sliding guide rail 12 more stably, to ensure a smooth and reliable movement for the movable block 15 on the sliding guide rail 12.

In this embodiment, as shown in FIG. 2 and FIG. 4, there are two parallel sliding guide rails 12 to be illustrated, and the movable block 15 is located between the two sliding guide rails 12, so that the movable block can be mounted more stably. One end of the movable block 15 which is cooperated with the sliding guide rails 12 is provided with four pulleys 28, two of which are respectively disposed on both sides of the sliding guide rails 12, so that the movable block can be mounted on the sliding guide rails 12 more stably and reliably.

In the present embodiment, as shown in FIG. 4, for example, the sliding portion 26 is movable relative to the movable block 15. The movement of the detector in the radial direction of the gantry is adjustable according to the cooperation between the sliding portion 26 and the sliding rail unit 27. Illustratively, the movement direction of the sliding portion 26 may be parallel to the movement direction of the movable block 15. Referring to FIG. 9, and taking an example shown in FIG. 8, if the two sliding portions 26 move in a direction away from each other (i.e., moving upward along the sliding guide rail 12), due to the connection between the sliding portions 26 and the movable block 15, and the movement of the sliding portions 26 drives the movable block 15 to move toward the axis center of the gantry along the radial direction thereof, that is, move from the solid line position to the dotted line position along the radial direction of the gantry.

Figure 7:
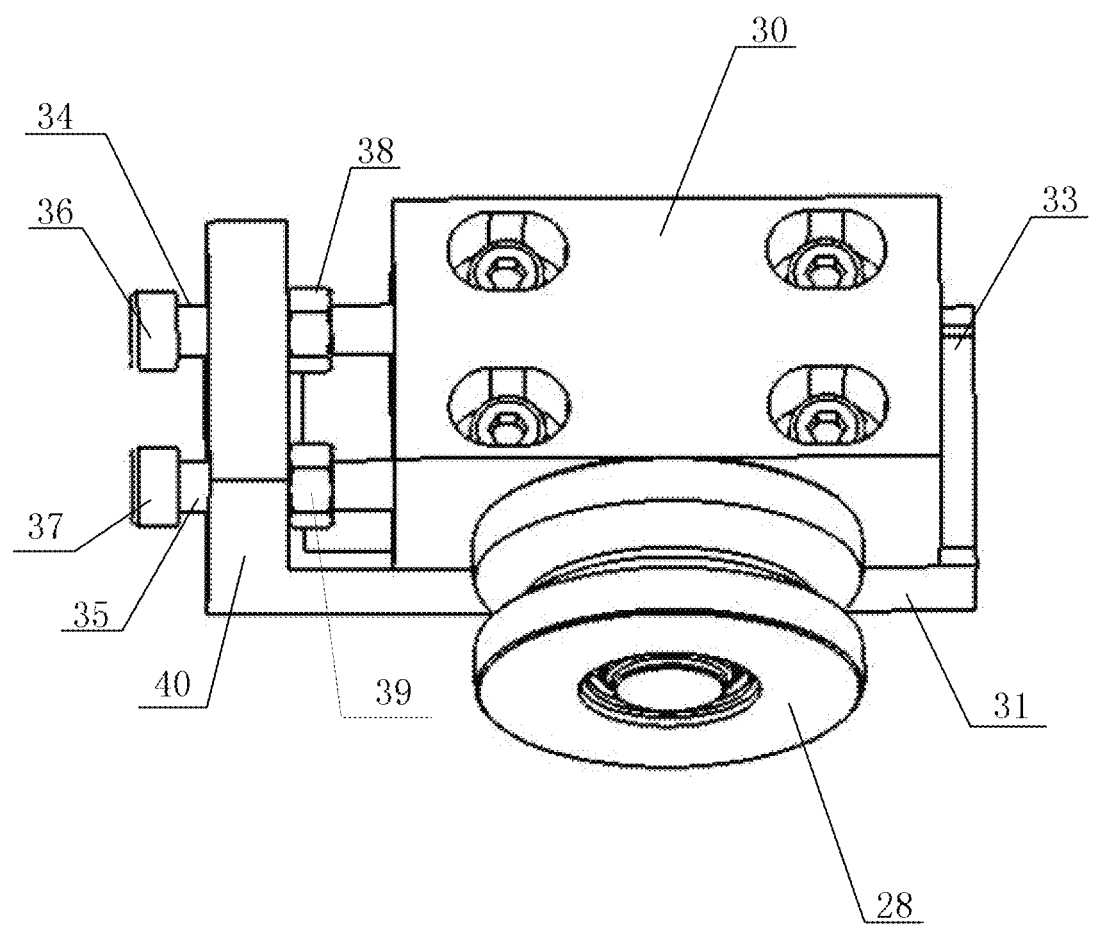
FIG. 7 is a schematic structural view of part of the radiotherapeutic device, according to another embodiment of the present disclosure.

As shown in FIGS. 4 and 7, for example, the movable block 15 is mounted with a mounting base 31, and the sliding portion 26 is disposed on the mounting base 31, the sliding portion 26 is movable relative to the mounting base 31. The sliding portion 26 is fixed to the movable plate 15 by the mounting base 31, so that the mounting and dismounting of the sliding portion 26 can be facilitated, and the adjustment of the sliding portion 26 is also facilitated.

Figure 6:
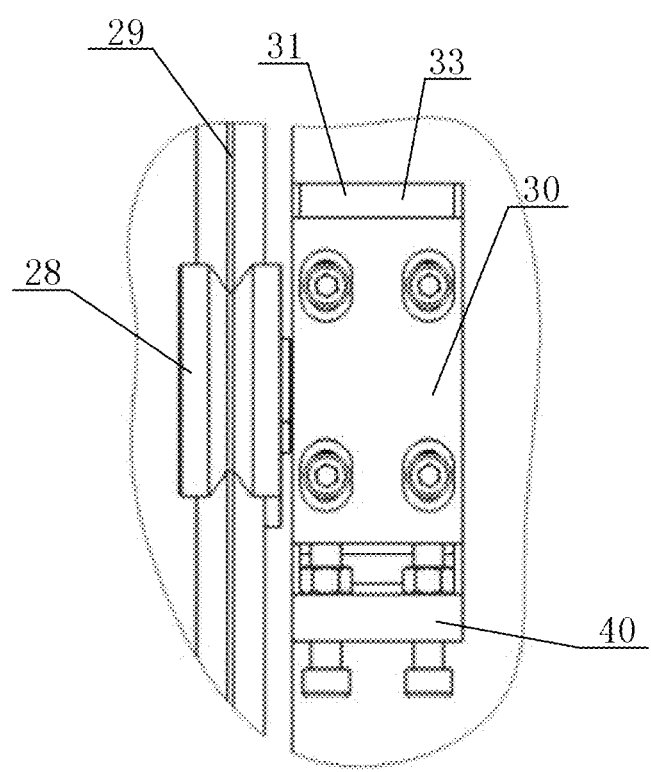
FIG. 6 is a schematic structural view of part of the radiotherapeutic device, according to an embodiment of the present disclosure.

As shown in FIGS. 6 and 7, for example, the sliding portion 26 further includes a pulley base 30, the pulley 28 is mounted on the pulley base 30, and the pulley base 30 is mounted on the mounting base 31. The pulley base 30 is movable relative to the mounting base 31. As such, the pulley 28 can be mounted on the pulley base 30 and then integrally mounted on the mounting base 31 to facilitate assembly. As shown in FIGS. 6 and 7, for example, the mounting base 31 is provided with a sliding groove 33, the pulley base 30 slides along the sliding groove 33. As such, the pulley base 30 can be moved in the sliding groove 33 to be adjusted.

Figure 8:
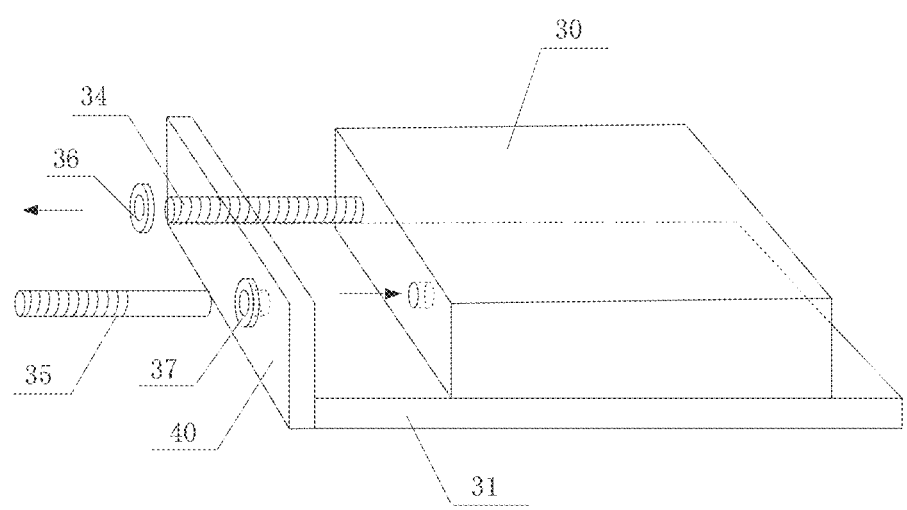
FIG. 8 is a schematic diagram showing the movement direction of a pulley base of the radiotherapeutic device, according to an embodiment of the present disclosure.
Figure 9:
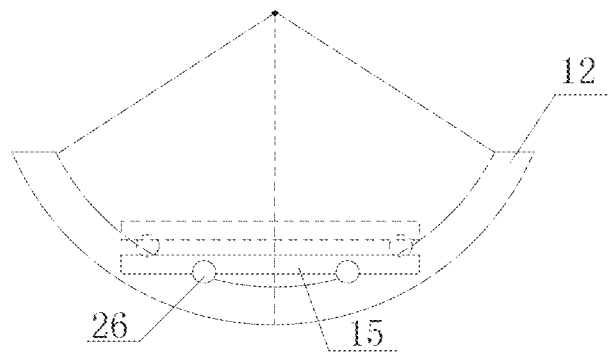
FIG. 9 is a schematic diagram showing an offset of the pulley base of the radiotherapeutic device in axis direction, according to an embodiment of the present disclosure.

In another embodiment of the present invention, preferably, as shown in FIGS. 7 and 8, the mounting base 31 is connected to a baffle through a locking assembly, the pulley base 30 is fixed or movable relative to the mounting base 31 with the force of the locking assembly. Preferably, the locking assembly comprises a first locking portion and a second locking portion, the direction of the force applied to the pulley base by the first locking portion is opposite to that of the second locking portion.

As an example, the mounting base 31 is provided with a baffle 40 having a hole. The first locking portion comprises at least one first tensional screw 34, one end of the first tensional screw 34 is connected to the pulley base 30 and the other end of the first tensional screw 34 passes through the hole of the baffle 40 to be limited therein. If the hole is provided with internal threads, the first tensional screw 34 is connected to the hole by threaded connection; alternatively, the first locking portion further includes a first nut 36, the first tensional screw 34 passes through the hole and then connects to the first nut 36.

The second locking portion comprises at least one second tensional screw 35, one end of the second tensional screw 35 is connected to the pulley base 30 and the other end of the second tensional screw 35 passes through the hole of the baffle 40 to be limited therein. If the hole is provided with internal threads, the second tensional screw 35 connected to the hole by threaded connection; alternatively, the second locking portion further includes a second nut 37, the second tensional screw 35 passes through the hole and then connects to the second nut 37.

Wherein, the direction of the force applied to the pulley base 30 by the first tensional screw 34 is opposite to that of the second tensional screw 35. For example, as shown in FIGS. 7 and 8, one end of the first tensional screw 34 is fixed to the pulley base 30, e.g., by weld or screw. The other end of the first tensional screw 34 passes through the hole in the baffle 40 and is fixed therein by a first nut 36. Force in the direction of the shown arrow (FIG. 8) is applied to the pulley base 30, to further restrict the movement of the pulley base 30 relative to the mounting base 31. One end of the second tensional screw 35 is in contact with the pulley base 30 and applies force to the pulley base 30 in the direction of the arrow (FIG. 8), and the other end thereof passes through the hole of the baffle 40 and is limited therein. Wherein, there is a second nut 37 is provided nearby the hole of the baffle 40, and the second tensional screw 35 is threadedly connected to the second nut 37, to restrict movement of the pulley base 30 relative to the mounting base 31.

In the embodiment of the present invention, as shown in FIGS. 7 and 8, since the direction of the force applied to the pulley base by the first tensional screws is opposite to that of the second tensional screws, by the way of "pulling and pushing" the first tensional screw and the second tensional screw respectively, namely: pushing the second tensional screws to the pulley base, and pulling out the first tensional screws from the pulley base, the pulley base can be limited to be no longer moveable along the direction of the groove. Finally, using nuts to lock the two tensional screws respectively, so that there is no relative displacement between the pulley and the L-shaped mounting base. The locking method makes the distance between the detector and the therapeutic head or the CT tube keep constant, and the ratio of the size of the image is always constant, it is easier to realize the accurate detection and control of the absorbed dose. Here, the locking assembly is not limited to screws, and the number of the tensional screws is not limited in the present invention, but only as an illustration.

It is further preferred that the first locking portion and/or the second locking portion further comprises a protection nut which is connected to the first tensional screw and/or the second tensional screw on the other side of the baffle. With reference to FIG. 7, take both the first and second locking portions including protection nut as an example, a first protection nut 38 is threadedly connected to the first tensional screw 34 on the other side of the baffle, a second protection nut 39 is threadedly connected to the second tension screw 35 on the other side of the baffle, to restrict the movement of the pulley base 30. As such, the position of the pulley base 30 can be further fixed when the position of the pulley base 30 in the sliding groove 33 is determined, thereby preventing an accidental positional change of the pulley base 30.

Illustratively, as shown in FIG. 3, the movable block 15 is provided with a cover plate 151, and the detector 16 is disposed between the movable block 15 and the cover plate 151. The cover plate 151 comprises a through hole 152 to expose the detector 16 to receive radiation. As such, the detector 16 can move with the movable block 15 to receive radiation.

For example, the detector is mounted on the movable block by a moving mechanism, to move along a radial direction of the gantry, to increase or decrease the distance from the movable block to the center of the gantry, thus adjusting the size of the beam on the detector. It should be noted that the moving mechanism allows the detector to move a greater distance in the radial direction of the gantry. To be exemplified, the moving mechanism can be mounted on a jacking device between the detector and the movable block. Of course, the moving mechanism may be located on one side surface of the detector, and the position of the moving mechanism and the movement manner of the detector are not specifically limited in the present invention.

Illustratively, the detector is mounted on the movable block through a driving mechanism, to move along an axial direction of the gantry. In this way, the position of the detector can be adjusted in the axial direction according to the position of the emission, so that the detector can receive the radiation more accurately. Illustratively, in the case where the detector is small, i.e. the detector is significantly smaller than the movable block, the detector can be moved on the movable block, making the detector more flexible. Preferably, the detector is moved between the two guide rails 12, i.e. moving along the axial direction of the gantry.

Figure 1:
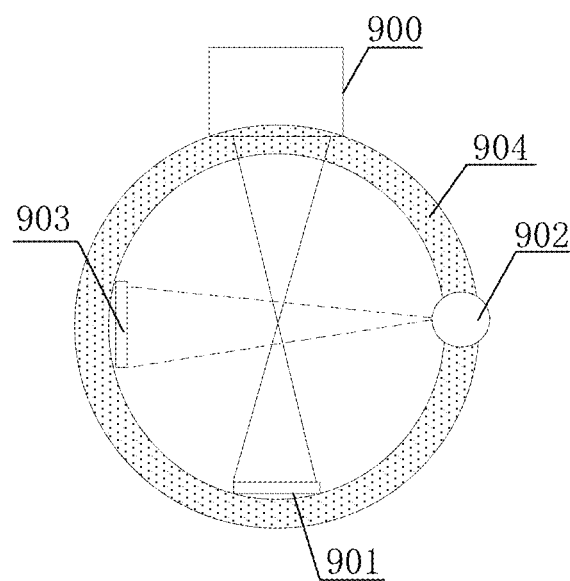
FIG. 1 is a schematic view of a radiotherapeutic device according to prior art.
Figure 10:
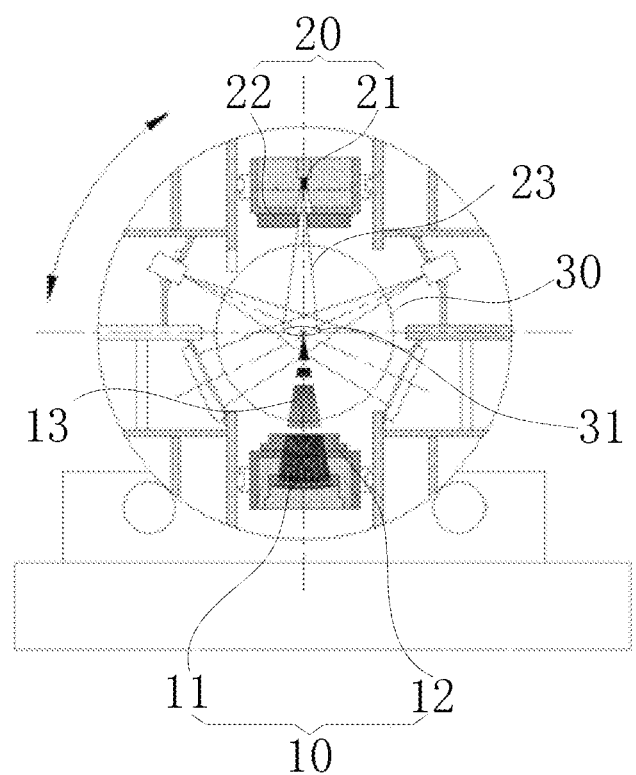
FIG. 10 is a schematic view of the radiotherapeutic device according to an embodiment of the present disclosure.
Figure 11:
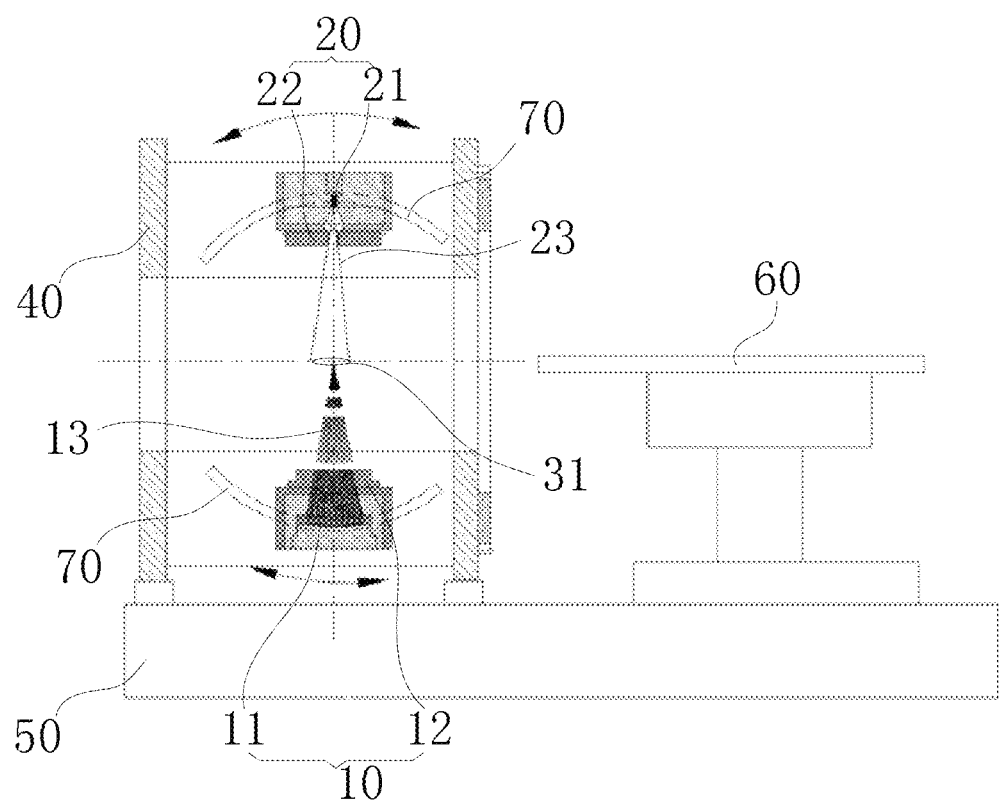
FIG. 11 is a side view of the radiotherapeutic device of FIG. 10.

In an embodiment of the invention, the radiotherapeutic device comprises at least one focused therapeutic head and at least one conformal therapeutic head. The radiotherapeutic device includes at least one focused therapeutic head and at least one conformal therapeutic head. For example, the radiotherapeutic device may include one focused therapeutic head and one conformal therapeutic head, or the radiotherapeutic device may include two focused therapeutic heads and one conformal therapeutic head, or alternatively, the radiotherapeutic device may be comprised of two focused therapeutic heads and two conformal therapeutic heads. As illustrated in FIGS. 10 and 11, the present application is illustrated with an example in which the radiotherapeutic device comprises a focused therapeutic head 10 and a conformal therapeutic head 20, as shown in FIGS. 1 and 2, in this embodiment, as an example, the focused therapeutic head 10 is disposed opposite the conformal therapeutic head 20.

A focused therapeutic head generally refers to a therapeutic head comprising a plurality of radioactive sources, all radioactive sources are focused on one focal point. The focal point can move to different regions of the tumor for performing treatment therein. A conformal therapeutic head generally refers to a therapeutic head comprising one radioactive source emitting a scattered cone beam, and a collimator or a multi-leaf collimator configured therein forming a beam-passable region similar to the shape of the tumor. The cone beam is irradiated to the tumor through the beam-passable region, thereby realizing the radiation therapy of the tumor.

Illustratively, referring FIGS. 10 and 11, the focused therapeutic head 10 includes a plurality of first radioactive sources 11 each being capable of emitting a first radiation beam 13. The field diameter of the first radiation beam 13 can be adjusted through a collimator 12. The plurality of first radiation beams 13 are focused on a focal point that is irradiated on a partial region of the tumor 31 of the human body 30. The conformal therapeutic head 20 includes a second radioactive source 21 that emits a scattered cone beam 23. A multi-leaf collimator 22 forms a beam-passable region which is similar to the tumor shape. As such, the tumor 31 can be irradiated by passing the cone beam 23 through the beam-passable region, to achieve the purpose of conformal treatment. Of course, the shape of the beam-passable region formed by the multi-leaf collimator can be changed in various forms, e.g. the beam-passable region may correspond to part of the tumor area, and the conformal irradiation area formed by the multi-leaf collimator is not limited to the present disclosure.

Of course, the radiotherapeutic device may include other components. For example, As shown in FIGS. 10 and 11, the radiotherapeutic device includes a base 50, a gantry 11, the therapeutic heads, and a treatment couch 60. The base 50 supports the whole radiotherapeutic device 100, and plays a role of carrying the whole radiotherapeutic device 100 and a role of fixation. The treatment couch 60 is arranged on the base 50, and is movably connected to the base 50, e.g. by screws and/or pins. The treatment couch 60 is used to support and position a patient, and can accurately deliver the patient to a specified position for treatment. The gantry 11 is arranged on the base 50, and is connected to the base 50 by a rolling support. The gantry 11 rotates around an axial line by means of, e.g. gear driving.

In embodiments of the present invention, the focused therapeutic head and/or the conformal therapeutic head are continuously translated around the focal point in an axial plane of the gantry to achieve non-coplanar focused and/or conformal treatment at different incident angles. Illustratively, the focused therapeutic head and/or the conformal therapeutic head are respectively connected to the gantry through an arc-shaped guide rail in the axial direction of the gantry, so that the focused therapeutic head and/or the conformal therapeutic head can continuously translate about the focal point in the axial plane of the gantry.

According to an embodiment of the present invention, the radiotherapeutic device further comprises a dynamic image guide system (IGS) comprising one or two sets of stereo imaging apparatuses assembled in fixed angles, to perform detection of a body position of a patient or spatial position of the lesion. Illustratively, an included angle of two sets of imaging apparatuses in the stereo imaging apparatus is in a range of 20 degrees to 160 degrees, and the stereo imaging apparatus includes X-ray generator(s) and image detector(s).

According to an embodiment of the present invention, a method of driving the radiotherapeutic device is disclosed. The radiotherapeutic device includes at least one first radiation head and a second radiation head, and the method comprises the following steps:

the driving apparatus drives the movable block to slide along the guide rail to a first position, to receive radiation beams emitted from the first radiation head;

the driving apparatus drives the movable block to slide along the guide rail to a second position, to receive radiation beams emitted from the first radiation head and/or the second radiation head.

In this way, it is possible to move the detector to a first position to receive the radiation beams from the first radiation head and to the second position to receive the radiation beams from the second radiation head, driven by the driving apparatus, with fewer detectors. Of course, the detector can be moved to other locations to receive the radiation beams from the other radiation heads, thereby enabling the use of fewer detectors to perform functions such as dose verification or image guidance in the radiotherapeutic device, saving a lot of treatment space. Meanwhile, fewer detectors can greatly reduce the acquisition cost of radiotherapeutic device and maintenance cost.

As an example, the method further comprises: adjusting the first locking portion such that the sliding portion is moved relative to the movable block. As a result, it is possible to adjust the sliding portion according to the cooperation between the sliding portion and the sliding guide rail, to fit different guide rails.

As an example, the method further comprises: the driving mechanism drives the detector to move along the axial direction of the gantry. In this way, the position of the detector can be adjusted in the axial direction, so that the detector can receive the radiation more accurately.

As an example, the method further comprises: the moving mechanism drives the detector to move along the radial direction of the gantry, to increase or decrease the distance from the movable block to the center of the gantry, thus adjusting the field size of the beam emitted on the detector.

As an example, the first radiation head and the second radiation head are therapeutic heads with MV-level radiation.

It is to be understood that the foregoing is intended only as a specific embodiment of the invention and is not intended to limit the scope of the invention. The scope of protection of the present invention is to be understood to be within the scope of the present invention as defined by the equivalents thereof or equivalents thereof or to any other related art, either directly or indirectly, by the use of the present specification and drawings.

I claim:

1. A radiotherapeutic device, comprising:
   a gantry, a detector and a slide driving unit, wherein the slide driving unit comprises a sliding guide rail, a driving apparatus and a movable block, the detector is fixed on the movable block, the movable block drives the detector to slide along the sliding guide rail driven by the driving apparatus;
   wherein the driving apparatus comprises a driver, a first motivation portion disposed on the movable block, and a second motivation portion disposed on the sliding guide rail, the first motivation portion cooperates with the second motivation portion to drive the movable block sliding along the sliding guide rail;
   the first motivation portion comprises a first motivation unit, the second motivation portion comprises a second motivation unit, the first motivation unit is connected to the movable block and the driver respectively, the second motivation unit is disposed on the sliding guide rail, and the driver drives the first motivation unit to move on the second motivation unit and further drives the movable block to slide along the sliding guide rail;
   the first motivation portion further comprises a sliding portion disposed on the movable block, and the second motivation portion further comprises a sliding rail unit mounted on the movable block, the sliding portion is cooperated with the sliding rail unit and slides relative to each other;
   the sliding portion is movable relative to the movable block;
   the movable block is mounted with a mounting base, and the sliding portion is disposed on the mounting base, the sliding portion is movable relative to the mounting base; and
   the sliding portion comprises at least one pulley slidable on the sliding guide rail.

2. The radiotherapeutic device of claim 1, wherein at least one sliding portion is disposed on each side of the sliding guide rail, and the two sliding portionson both sides sandwich the sliding guide rail.

3. The radiotherapeutic device of claim 1, wherein the sliding rail unit comprises at least one groove disposed on the sliding guide rail, and the pulley is provided with a flange which engages with the groove; or the pulley is provided with at least one groove, and the sliding rail unit comprises a flange disposed on the sliding guide rail that engages the groove.

4. The radiotherapeutic device of claim 1, wherein the sliding portion further comprises a pulley base, the pulley is mounted on the pulley base, the pulley base is mounted on the mounting base, and the pulley base is movable relative to the mounting base.

5. The radiotherapeutic device of claim 4, wherein the mounting base is provided with a groove, the pulley base slides along the groove.

6. The radiotherapeutic device of claim 5, wherein a locking assembly is disposed on the mounting base, the pulley base is fixed or movable relative to the mounting base under the force of the locking assembly.

7. The radiotherapeutic device of claim 1, wherein a cover plate is disposed on the movable block, and the detector is disposed between the movable block and the cover plate, the cover plate comprises a through hole to expose the detector to receive radiation.

8. The radiotherapeutic device of claim 1, wherein the detector is mounted on the movable block by a moving mechanism, to move along a radial direction of the gantry.

9. The radiotherapeutic device of claim 1, wherein the detector is mounted on the movable block through a driving mechanism, to move along an axial direction of the gantry.

10. The radiotherapeutic device of claim 1, wherein the detector and the slide driving unit are disposed on the inner side of the gantry; and
    the sliding guide rail is arc shaped, and the center of the sliding guide rail coincides with the center of the gantry.

11. The radiotherapeutic device of claim 1, further comprising: a radiation head for emitting γ rays.

12. The radiotherapeutic device of claim 1, further comprising: a radiation head for emitting rays in MV-level.

13. A radiotherapeutic device, comprising:
    a gantry, a detector, at least two radiation heads and a slide driving unit, wherein the slide driving unit comprises a sliding guide rail, a driving apparatus and a movable block, the detector is fixed on the movable block, the movable block drives the detector to slide along the sliding guide rail driven by the driving apparatus, and receive rays emitted by the radiation heads;
    wherein the driving apparatus comprises a driver, a first motivation portion disposed on the movable block, and a second motivation portion disposed on the sliding guide rail, the first motivation portion cooperates with the second motivation portion to drive the movable block sliding along the sliding guide rail;
    the first motivation portion comprises a first motivation unit, the second motivation portion comprises a second motivation unit, the first motivation unit is connected to the movable block and the driver respectively, the second motivation unit is disposed on the sliding guide rail, and the driver drives the first motivation unit to move on the second motivation unit and further drives the movable block to slide along the sliding guide rail;
    the first motivation portion further comprises a sliding portion disposed on the movable block, and the second motivation portion further comprises a sliding rail unit mounted on the movable block, the sliding portion is cooperated with the sliding rail unit and slides relative to each other;
    he sliding portion is movable relative to the movable block;

the movable block is mounted with a mounting base, and
the sliding portion is disposed on the mounting base,
the sliding portion is movable relative to the mounting base; and
the sliding portion comprises at least one pulley slidable on the sliding guide rail.

14. The radiotherapeutic device of claim 13, wherein the at least two radiation heads comprise a therapeutic head and an imaging head.

15. The radiotherapeutic device of claim 13, wherein the at least two radiation heads comprise a focused therapeutic head and a conformal therapeutic head.

* * * * *